United States Patent
Vargas-Garza

[19]

[11] Patent Number: 5,258,557
[45] Date of Patent: Nov. 2, 1993

[54] PROCESS FOR THE PREPARATION OF CHELATANT ORGANIC ACIDS

[76] Inventor: Hector Vargas-Garza, Ave. Junco de la Vega #208, Colonia, Roma 64700, Monterrey, Nuevo Leon, Mexico

[21] Appl. No.: 958,753

[22] Filed: Oct. 9, 1992

[51] Int. Cl.$^5$ ............................................. C07C 51/00
[52] U.S. Cl. ........................................ 562/515; 554/8
[58] Field of Search ................. 554/8; 562/515, 523

[56] References Cited

U.S. PATENT DOCUMENTS

| | | | |
|---|---|---|---|
| 1,941,760 | 1/1934 | Rinman | 554/8 X |
| 2,065,848 | 12/1936 | Anderson | 554/8 X |
| 2,299,603 | 10/1942 | Thurman | 554/8 X |
| 2,337,034 | 12/1943 | Davis | 554/8 X |

Primary Examiner—Arthur C. Prescott
Attorney, Agent, or Firm—Laurence R. Brown

[57] ABSTRACT

This invention relates to a Process for the preparation of Chelatant Organic Acids, from Pentosanes contained in corn husk, wheat seed husk, rice seed husk, oat seed husk, barley seed husk, cotton seed husk, sorgus seed husk, buffel, alfalfa and similar pastures, and harvests and residues of such.

11 Claims, No Drawings

PROCESS FOR THE PREPARATION OF CHELATANT ORGANIC ACIDS

DESCRIPTION OF THE INVENTION

This invention has the objective of preparing Chelatant Organic Acids, from the Pentosanes contained in corn husk, and seeds of wheat, rice, oats, barley, cotton and sorgus, harvests, and residues of buffel and alfalfa pastures; which are first mixed in a water solution where a 65% concentrate of Nitric Acid in 10% proportion has been previously added and heated to a boil.

Once the corn or seed husks, or the pastures or residues of said vegetables have oxidized in the boiling solution vigorously mixing during two hours, the Chelatant Organic Acids will be produced.

EXAMPLE

In a stainless steel container add 350 liters of water and 50 liters of 65% concentrate Nitric Acid and heat the mixture to a boil.

Once the boiling point is reached, add 100 kilos of corn husk, or the husks from seeds of oats, wheat, barley, cotton, sorgus, buffel or alfalfa pasture, or residues of such vegetables, which contain, any of the beforementioned, in their structure a Pentosane.

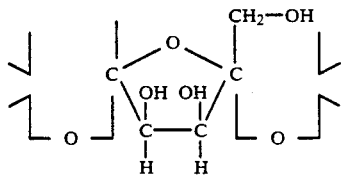

Oxidizing the contents for two hours at boiling temperatures while vigorously mixing, results in a series of Chelatant Organic Acids:

$H_2O + HNO_3 + PENTOSANE \rightarrow CHELATANT$ ORGANIC ACIDS

The liquid is separated from the solid material by simple filtration resulting in Chelatant Organic Acids in liquid form.

USE OF THE RESULTING PRODUCT, CHELATANT ORGANIC ACIDS

Some of the resulting Chelatant Organic Acid namely: Oxalic Acid $C_2O_4H_2$, Saccharic Acid $CH_3CH=CHCOOH$, Gluconic Acid $CH_2OH(CHOH)_4COOH$, Glucharic Acid $(CHOH)4$, Tryoxiglucharic Acid $(CHOH)_3(COOH)_2$, etc. can be mixed with some alkaline compound for its pH neutralization like for example: Calcium Hydroxide $Ca(OH)_2$, Potassium hydroxide K OH, Ferrus Hydroxide $Fe(OH)_2$, Copper hydroxide $Cu(OH)_2$, Magnesium Hydroxide $(Mg(OH)_2$, Cobalt hydroxide $Co(OH)_2$, Aluminum Hydroxide $Al(OH)_2$, Strontium hydroxide $Sr(OH)_2$, Nickel Hidroxide $Ni(OH)_2$, Sodium hydroxide $Na(OH)_2$, etc. In the previous examples, if Calcium hydroxide $Ca(OH)_2$, is used, this will be added to the Chelatant Organic Acids until a pH of between 7 and 7.5 is reached, resulting the Calcium Chelates corresponding to in Chelatant Organic Acids before mentioned, which if applied to the human skin act as an anti-inflammatory penetrating the cells of the skin reducing the Histamine in the inflammated area. If Potassium Hydroxide K OH, is used, this will be added to the Chelatant Organic Acids until the pH is raised to between 7 and 7.5, resulting in the corresponding Potassium Chelates of the Chelatant Organic Acids mentioned previously which if applied to the human skin will act as an anti-inflammatory and anti-septic penetrating in the sebaceous glands eliminating the obstruction caused by the purulence formed by infection normally called blackhead.

What is claimed is:

1. A process for the preparation of chelatant organic products from pentosanes contained in raw materials comprising corn husks and husks from the seed of wheat, rice, oats, barley, cotton, sorgus, buffel, alfalfa and similar pastures, characterized by the steps of putting water into a stainless steel container, adding a 65% concentrate of Nitric Acid in 10% proportion, mixing well and heating these contents to a boiling point; when boiling, adding to the contents a 20% proportion by volume of said raw materials to provide a mixture, boiling said mixture for the order of two hours while vigorously mixing until oxidizing takes place and chelatant organic acids are produced.

2. The process of claim 1 further comprising the step of converting the produced chelatant organic acid to calcium chelates by adding Calcium Hydroxide—$Ca(OH)_2$—until the pH is raised to between 7 and 7.5.

3. The process of claim 1 further comprising the step of converting the produced chelatant organic acid to potassium chelates by adding Potassium Hydroxide—$K(OH)_2$—until the pH is raised to between 7 and 7.5.

4. The process of claim 1 further comprising the step of converting the produced chelatant organic acid to ferrous chelates by adding ferrous Hydroxide—$Fe(OH)_2$—until the pH is raised to between 7 and 7.5.

5. The process of claim 1 further comprising the step of converting the produced chelatant organic acid to copper chelates by adding Copper Hydroxide—$Cu(OH)_2$—until the pH is raised to between 7 and 7.5.

6. The process of claim 1 further comprising the step of converting the produced chelatant organic acid to magnesium chelates by adding Magnesium Hydroxide—$Mg(OH)_2$—until the pH is raised to between 7 and 7.5.

7. The process of claim 1 further comprising the step of converting the produced chelatant organic acid to cobalt chelates by adding Cobalt Hydroxide—$CO(OH)_2$—until the pH is raised to between 7 and 7.5.

8. The process of claim 1 further comprising the step of converting the produced chelatant organic acid to aluminum chelates by adding Aluminum Hydroxide—$Al(OH)_3$—until the pH is raised to between 7 and 7.5.

9. The process of claim 1 further comprising the step of converting the produced chelatant organic acid to strontium chelates by adding Strontium Hydroxide—$Sr(OH)_2$—until the pH is raised to between 7 and 7.5.

10. The process of claim 1 further comprising the step of converting the produced chelatant organic acid to nickel chelates by adding Nickel Hydroxide—$Ni(OH)_2$—until the pH is raised to between 7 and 7.5.

11. The process of claim 1 further comprising the step of converting the produced chelatant organic acid to sodium chelates by adding Sodium Hydroxide—$NaOH$—until the pH is raised to between 7 and 7.5.

* * * * *